US009158376B2

(12) United States Patent
Kazerooni et al.

(10) Patent No.: US 9,158,376 B2
(45) Date of Patent: Oct. 13, 2015

(54) USER COUPLED HUMAN-MACHINE INTERFACE

(71) Applicants: Homayoon Kazerooni, Berkeley, CA (US); Yoon Jung Jeong, Berkeley, CA (US); Kyunam Kim, Albany, CA (US)

(72) Inventors: Homayoon Kazerooni, Berkeley, CA (US); Yoon Jung Jeong, Berkeley, CA (US); Kyunam Kim, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/291,101

(22) Filed: May 30, 2014

(65) Prior Publication Data

US 2014/0358290 A1    Dec. 4, 2014

Related U.S. Application Data

(60) Provisional application No. 61/828,885, filed on May 30, 2013.

(51) Int. Cl.
    G05B 15/02    (2006.01)
    G06F 3/01     (2006.01)
    A61F 4/00     (2006.01)
    B25J 9/00     (2006.01)
    A61H 1/00     (2006.01)
    A61H 1/02     (2006.01)

(52) U.S. Cl.
    CPC . *G06F 3/014* (2013.01); *A61F 4/00* (2013.01); *A61H 1/00* (2013.01); *B25J 9/0006* (2013.01); *G05B 15/02* (2013.01); *G06F 3/011* (2013.01); *A61H 1/0262* (2013.01); *A61H 2201/1652* (2013.01); *A61H 2203/0406* (2013.01)

(58) Field of Classification Search
    None
    See application file for complete search history.

(56) References Cited

U.S. PATENT DOCUMENTS

| 6,097,369 | A  | * | 8/2000  | Wambach | 345/158 |
|-----------|----|----|---------|---------|---------|
| 6,128,004 | A  | * | 10/2000 | McDowall et al. | 345/158 |
| 6,154,199 | A  |   | 11/2000 | Butler |  |
| 6,681,638 | B2 |   | 1/2004  | Kazerooni et al. |  |
| 7,042,438 | B2 | * | 5/2006  | McRae et al. | 345/156 |

(Continued)

FOREIGN PATENT DOCUMENTS

| WO | WO 2012/027336 A1 | * | 3/2012 |
| WO | WO 2012/037555 A1 | * | 3/2012 |
| WO | WO 2012/048123 A1 | * | 4/2012 |

OTHER PUBLICATIONS

Hasegawa, Y.; Junho Jang; Sankai, Y., "Cooperative walk control of paraplegia patient and assistive system," Intelligent Robots and Systems, 2009. IROS 2009. IEEE/RSJ International Conference on, pp. 4481,4486, Oct. 10-15, 2009.*

(Continued)

*Primary Examiner* — Darrin Dunn
*Assistant Examiner* — Christopher E Everett
(74) *Attorney, Agent, or Firm* — Roberts Mlotkowski Safran & Cole, PC

(57) ABSTRACT

An input device for commanding an exoskeleton worn by a person, adapted to be coupled to the person, the input device comprising: at least one signal generator adapted to be coupled to the user's finger capable of generating at least one electric signal when said one signal generator gets contacted and, an input device controller adapted to be coupled to the user's body capable of receiving and processing at least one signal and transmitting a command signal to the exoskeleton.

20 Claims, 10 Drawing Sheets

(56) References Cited

U.S. PATENT DOCUMENTS

| | | | |
|---|---|---|---|
| 7,057,604 | B2 | 6/2006 | Bajramovic |
| 7,153,242 | B2 | 12/2006 | Goffer |
| 7,628,766 | B1 | 12/2009 | Kazerooni et al. |
| 7,947,004 | B2 | 5/2011 | Kazerooni et al. |
| 8,035,629 | B2 * | 10/2011 | Daniel ................. 345/204 |
| 8,622,938 | B2 * | 1/2014 | Sankai ................. 601/5 |
| 8,648,805 | B2 * | 2/2014 | Bailen ................. 345/163 |
| 8,681,101 | B1 * | 3/2014 | Haney et al. ................. 345/161 |
| 2002/0067342 | A1 * | 6/2002 | Proper ................. 345/163 |
| 2002/0175894 | A1 * | 11/2002 | Grillo ................. 345/156 |
| 2006/0260620 | A1 | 11/2006 | Kazerooni et al. |
| 2007/0056592 | A1 | 3/2007 | Angold et al. |
| 2009/0036804 | A1 * | 2/2009 | Horst ................. 601/5 |
| 2010/0094188 | A1 * | 4/2010 | Goffer et al. ................. 602/23 |
| 2011/0066088 | A1 | 3/2011 | Little et al. |
| 2013/0158445 | A1 * | 6/2013 | Kazerooni et al. ................. 601/35 |
| 2013/0231595 | A1 * | 9/2013 | Zoss et al. ................. 601/34 |
| 2013/0237884 | A1 * | 9/2013 | Kazerooni et al. ................. 601/34 |

OTHER PUBLICATIONS

Caldwell, D.G.; Kocak, O.; Andersen, U., "Multi-armed dexterous manipulator operation using glove/exoskeleton control and sensory feedback," Intelligent Robots and Systems 95. 'Human Robot Interaction and Cooperative Robots', Proceedings. 1995 IEEE/RSJ International Conference on , vol. 2, pp. 567,572 vol. 2, Aug. 5-9, 1995.*

Caldwell, D.G.; Gosney, C., "Enhanced tactile feedback (tele-taction) using a multi-functional sensory system," Robotics and Automation, 1993. Proceedings., 1993 IEEE International Conference on , pp. 955,960 vol. 1, May 2-6, 1993.*

Kazerooni, H.; Fairbanks, D.; Chen, A.; Shin, G., "The magic glove," Robotics and Automation, 2004. Proceedings. ICRA '04. 2004 IEEE International Conference on , vol. 1, No., pp. 757-763, vol. 1, Apr. 26-May 1, 2004.*

Eun-Hye Jang et al., Development of a Bio/Kinesthetic Sensor Fusion System for Walking-Support Exoskeletons, Nov. 2010, pp. 227-230, http://www.dbpia.co.kr/Journal/ArticleDetail/2929670.*

* cited by examiner

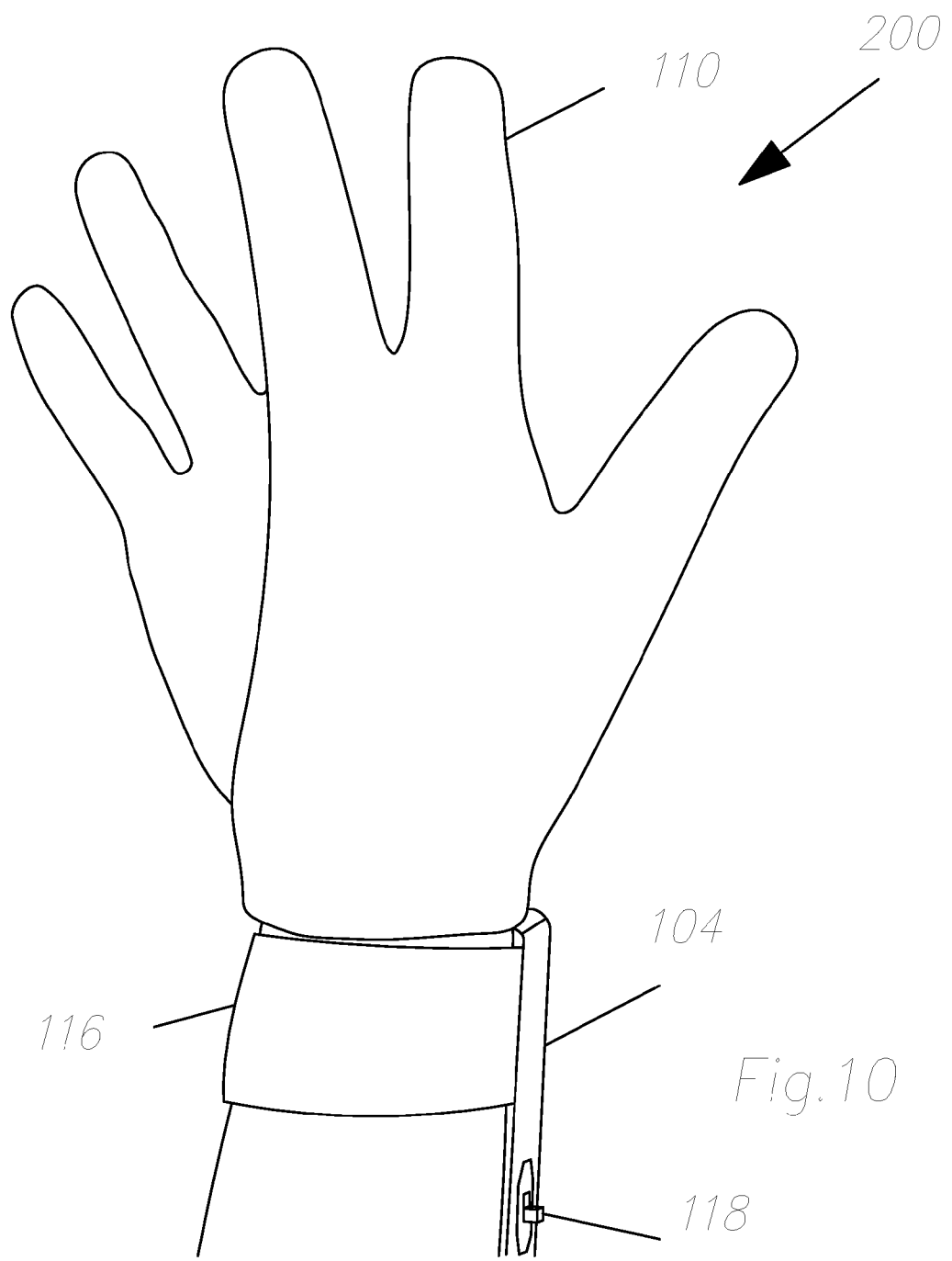

USER COUPLED HUMAN-MACHINE INTERFACE

BACKGROUND OF THE INVENTION

1. Technical Field

The present invention pertains to the art of controlling exoskeleton systems, and more particularly, to a control system which is adapted to be coupled to a person.

2. Discussion of the Prior Art

Patients who have difficulty walking often use wheelchairs for mobility. It is a common and well-respected opinion in the field that postponing the use of wheelchairs will retard the onset of other types of secondary disabilities and diseases. The ramifications of long-term wheelchair use are secondary injuries including hip, knee, and ankle contractures, heterotopic ossification of lower extremity joints, frequent urinary tract infection, spasticity, and reduced heart and circulatory function. These injuries must be treated with hospital care, medications, and several surgical procedures. Physicians strongly advocate the idea that it is essential for patients to forgo the use of wheelchairs and remain upright and mobile as much as possible.

Functional Electrical Stimulation (FES) is primarily used to restore function in people with disabilities. FES is a technique that uses electrical currents to activate muscles in lower extremities affected by paralysis resulting from spinal cord injury (SCI), head injury, stroke and other neurological disorders. The patient wears a set of orthosis for stability. An electrical stimulator is always in the "off" mode except when the patient decides to walk. By triggering a mini-switch mounted on each handlebar of a rolling walker, the patient activates one or some of the quadriceps and hamstrings and muscles. The trigger signal from the switch is transmitted to the stimulator via a cable from the walker. The pulsed current is applied to the patient via conventional carbon-impregnated rubber electrodes covered with solid gel. The book titled "Functional Electrical Stimulation: Standing and Walking After Spinal Cord Injury", Alojz R. Kralj, Tadej Bajd, CRC Press 1989, describes various technologies associated with FES. Another informative reference is "Current Status of Walking Orthoses for Thoracic Paraplegics", published in The Iowa Orthopedic Journal by D'Ambrosia.

Another ambulation method uses powered exoskeleton systems. Most powered medical exoskeletons include interface devices that allows a user to command the exoskeleton, such that the user's decision on which leg to move and how to move it is reflected in the motion of the exoskeletons through them.

Currently, there are different types of user interface for commanding exoskeletons. For instance, U.S. Patent Application Publication No. 2011/0066088 A1, incorporated herein by reference, discloses an exoskeleton with a mechanically connected interface device that consists of a joystick and a keypad, which are used as a user input means to input control instructions to the exoskeleton's control system. Drawbacks of this device are that it is bulky and it requires the user's arm to be coupled with part of the exoskeleton. U.S. Pat. No. 7,153,242, incorporated herein by reference, discloses a gait-locomotor apparatus with a Man-Machine Interface through which a user controls modes of operation and parameters of the device, and receives various indications. However, each motion of the apparatus is triggered by a control unit, not directly by a user, based on measurements from various sensors. This limits the user's control capability of the apparatus, and requires a number of sensors to be installed on the apparatus.

Accordingly, a need remains in the art for a simpler, more versatile interface device for control of various exoskeletons. One solution is to exploit an instrumented glove as an interface device. Currently, instrumented gloves are used in various applications. For example, attempts to use such gloves as computer mice are described in U.S. Pat. Nos. 7,057,604 B2, and 6,154,199. Moreover, U.S. Pat. No. 6,681,638 B2, discloses an instrumented glove device that is adapted to wireless material handling systems.

Yet, no prior art instrumented glove type device has been designed for exoskeleton interface devices. Further, many such devices are user input devices with actuating mechanisms on the palm of a user's hand, which would be undesirable if a user were required to utilize the palm of the hand for another purpose, such as leaning on a cane or other balancing aid. The present invention discloses an interface device that is worn on a user's hand. Furthermore, in the present invention, the instrumented glove is reduced to finger sleeve type signal generators. This structure of the present invention minimizes the hindrance of a user's hand movement caused by the glove. Furthermore, the present invention maximizes a user's capability to control an exoskeleton, as well as provides feedback signals from the exoskeleton.

SUMMARY OF THE INVENTION

This patent application describes an input device for commanding an exoskeleton worn by a person. The input device is adapted to be coupled to a person. The input device comprises at least one signal generator which is adapted to be coupled to a person's finger. The signal generator is capable of generating at least one electric signal when the signal generator gets contacted. The input device also comprises an input device controller which is adapted to be coupled to a person's body. In operation, an input device controller receives and processes at least one electric signal and transmits a command signal to the exoskeleton to perform a function. In some embodiments, at least one wire transmits at least one electric signal to the input device controller. In some embodiments of the invention two or more signal generators can be coupled to a finger. In some embodiments of the invention, the signal generator can be coupled to a practitioner's finger and the practitioner can generate at least one command signal to the exoskeleton to perform a function.

BRIEF DESCRIPTION OF DRAWINGS

FIG. 10 depicts a schematic of the glove where it covers at least two fingers.

MODES FOR CARRYING OUT THE INVENTION

Figure 1:
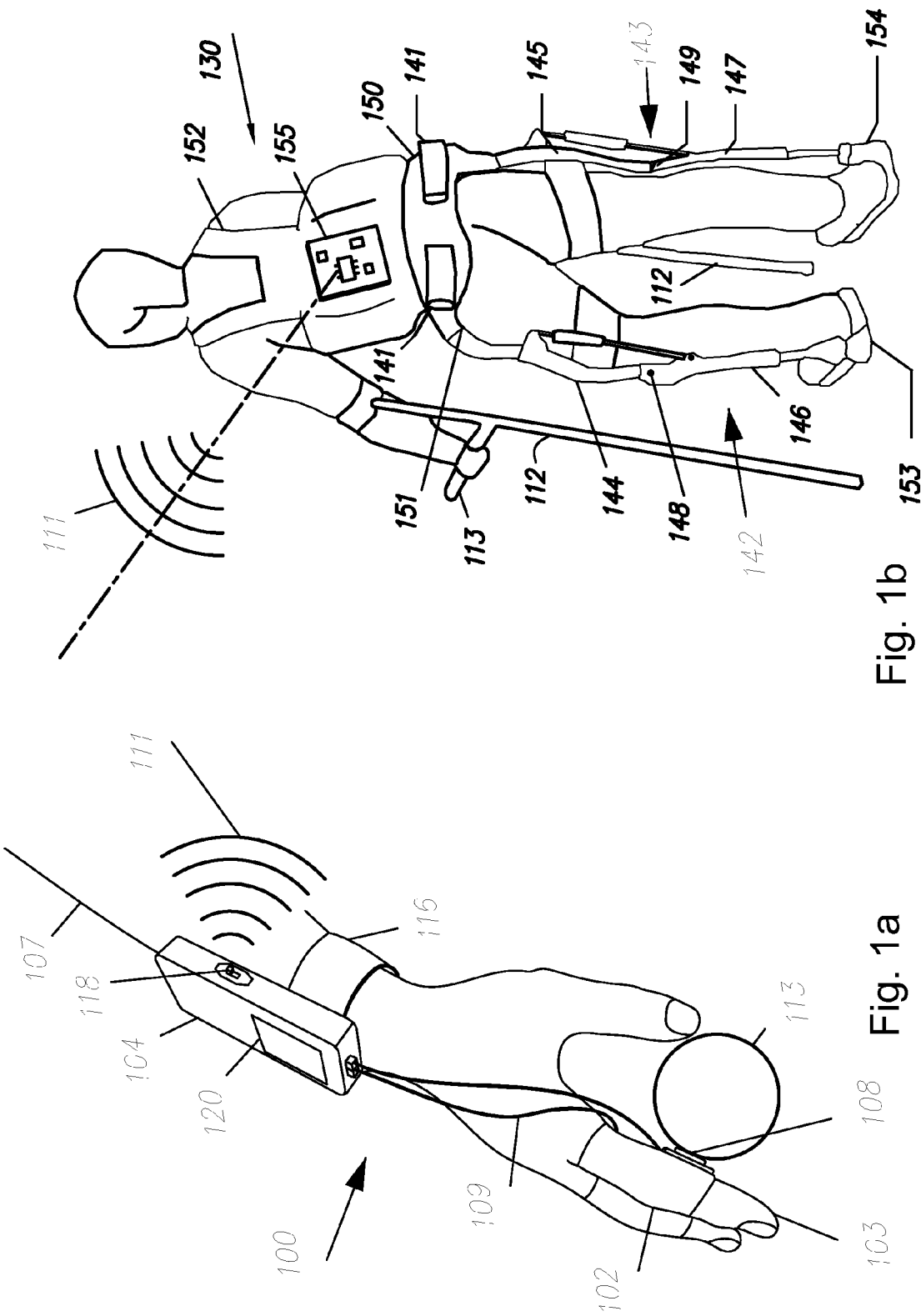
FIG. 1a depicts a user interface device of the present invention.
FIG. 1b depicts a rear perspective view of a powered exoskeleton system worn by a user, controlled by the present invention.

A first embodiment of an exoskeleton system for use with the present invention is generally indicated at 130 in FIG. 1b. In general, exoskeleton system 130 includes powered actuators 141 configured to be coupled to a person, and a separate support device 112 to provide the person with additional stabilization. By "separate" it is meant that exoskeleton 130 and support device 112 are not integrally or permanently connected, such that any number of different types of support devices 112 could be paired with any number of different types of exoskeleton devices, depending on the needs and limitations of a particular user. It should be understood that various different types of powered exoskeletons could be adapted for use with the present invention. Such exoskeletons are powered and allow the wearers to walk upright without any substantial energetic drain. Various mechanical architectures for the exoskeleton systems may have different degrees of freedom and actuations.

In some embodiments, the exoskeletons are powered electrically and some are powered hydraulically. U.S. Pat. No. 7,628,766 describes one example of a lower extremity exoskeleton system. Additionally, U.S. Patent Application Publication Nos. 2007/0056592 and 2006/0260620 teach various architectures of lower extremities.

In the embodiment depicted in FIG. 1b, exoskeleton 130 is configured for use by paraplegics for locomotion and includes first and second leg supports 142 and 143 configured to be coupled to the person's lower limbs and rest on a support surface during a stance phase. Each of the first and second leg supports includes a thigh link 144, 145 and a shank link 146, 147 interconnected by a knee joint 148, 149. Actuators 141 are adapted to apply torque to the leg supports 142, 143. An exoskeleton trunk 150 is configured to be coupled to a person's upper body and rotatably connects to respective first and second leg supports 142 and 143 at hip joints indicated at 151. Exoskeleton trunk 150 is preferably in the form of a supportive back frame. The attachment means utilized to connect exoskeleton trunk 150 to the person may be direct, such as strapping the user directly to the back frame via straps 152, or indirect, such as through a detachable harness (not shown) worn by the user which engages the back frame. Additionally, two foot links are connected to the distal ends of the leg supports 142 and 143. Exoskeleton 130 further includes an exoskeleton controller 155 which communicates with actuators 141 to shift exoskeleton 130 between various operational states, such as a Standing State, a Walking State and a Seated State. It should be readily understood that in a Standing State exoskeleton 130 and the user are in a standing position, in a Walking State exoskeleton 130 and the user are walking and in a Seated State exoskeleton 130 and the user are seated. Exoskeleton 130 can include various other elements such as multiple articulating joints that allow the movement of a user's lower extremities to be closely followed, additional actuators and sensors. However, unlike known powered exoskeleton devices, exoskeleton 130 includes an exoskeleton controller 155 that is configured to receive and respond to signals generated by user input device 100.

In the first embodiment, support device 112 is in the form of a set of first and second crutches, wherein each of the first and second crutches includes a handle indicated at 113. Although a set of crutches is depicted, it should be understood that a user could utilize only one crutch at a time.

In accordance with the present invention, a user input device signal generator 100 shown in FIG. 1a is configured to generate and send a user command signal generally indicated at 111 to exoskeleton controller 155. In response to user command signal 111, exoskeleton controller 155 causes exoskeleton 130 to shift between various operational states, as will be discussed in more detail below. User command signals 111 can be sent wirelessly, as depicted in FIG. 1a, or via a wired connection (not depicted).

Input device 100 in FIG. 1a is adapted to be coupled to a person. Input device 100 comprises at least one signal generator 102 which is adapted to be coupled to a person's finger 103. Signal generator 102 is capable of generating at least one electric signal when signal generator 102 contacts a balancing aid handle 113. Input device 100 also comprises an input device controller 104, adapted to be coupled to a user's body 107. In operation, input device controller 104 receives and processes at least one electric signal and transmits a command signal 111 to exoskeleton 130. In some embodiments, at least one wire 109 transmits at least one electric signal to input device controller 104. Although FIG. 1a shows input device 100 with two signal generators coupled to two fingers, it should be understood that additional signal generators 102 can be utilized with input device 100. In some embodiments of the invention two or more signal generators 102 can be coupled to a finger. Although FIG. 1 shows that input device controller 104 transmits a command signal 111 wirelessly, one can use wires and/or cables to transmit command signal 111 to exoskeleton 130. Signal generator 102 and input device controller 104 may be coupled to the same person's finger and body, or alternatively, signal generator 102 may be coupled to a practitioner and the practitioner can generate a command signal 111 to command exoskeleton 130 while input device controller 104 is coupled to another person wearing exoskeleton 130.

Figure 2:
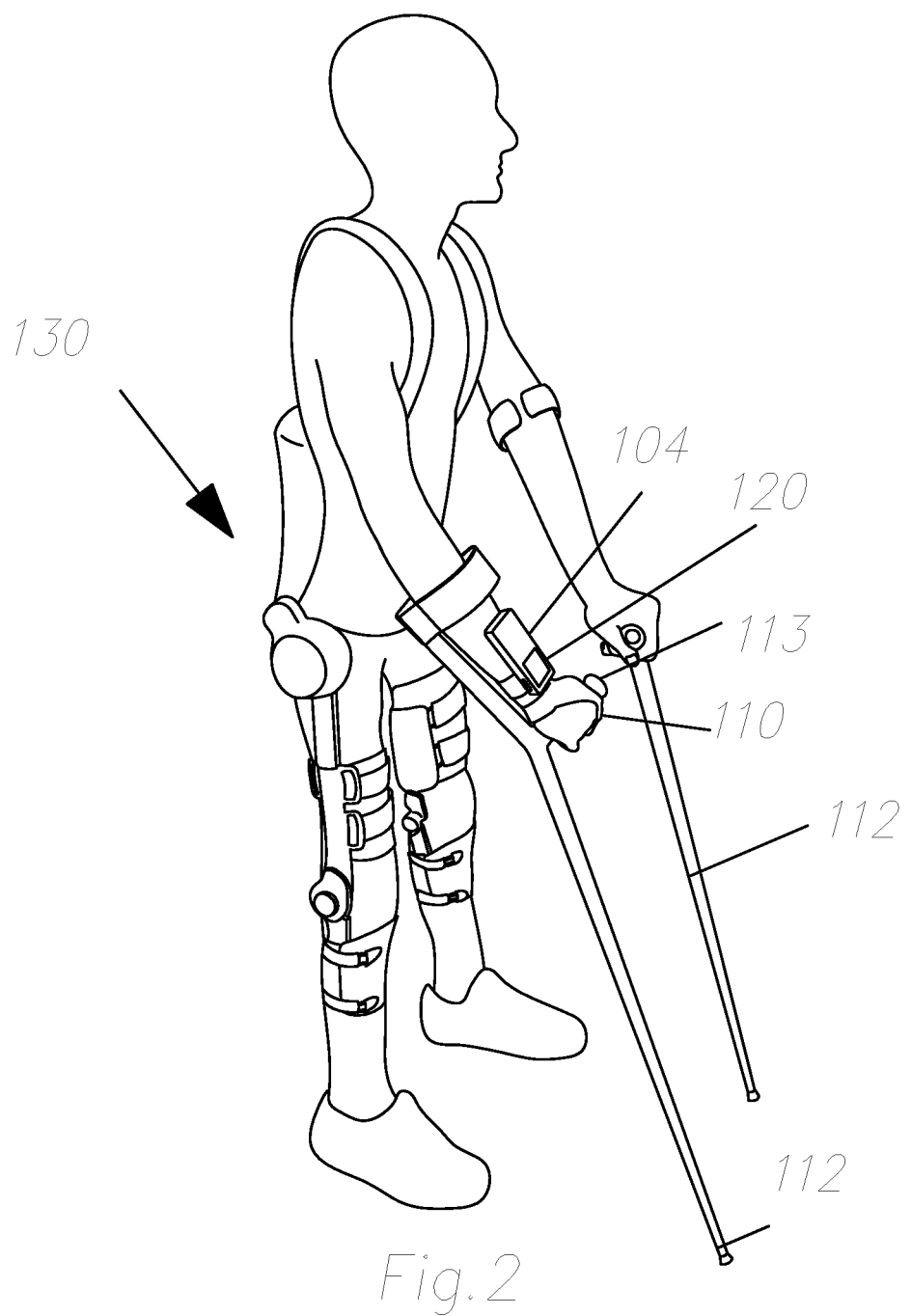
FIG. 2 depicts a user wearing an exoskeleton device, adapted to be controlled by the present invention.
Figure 3:
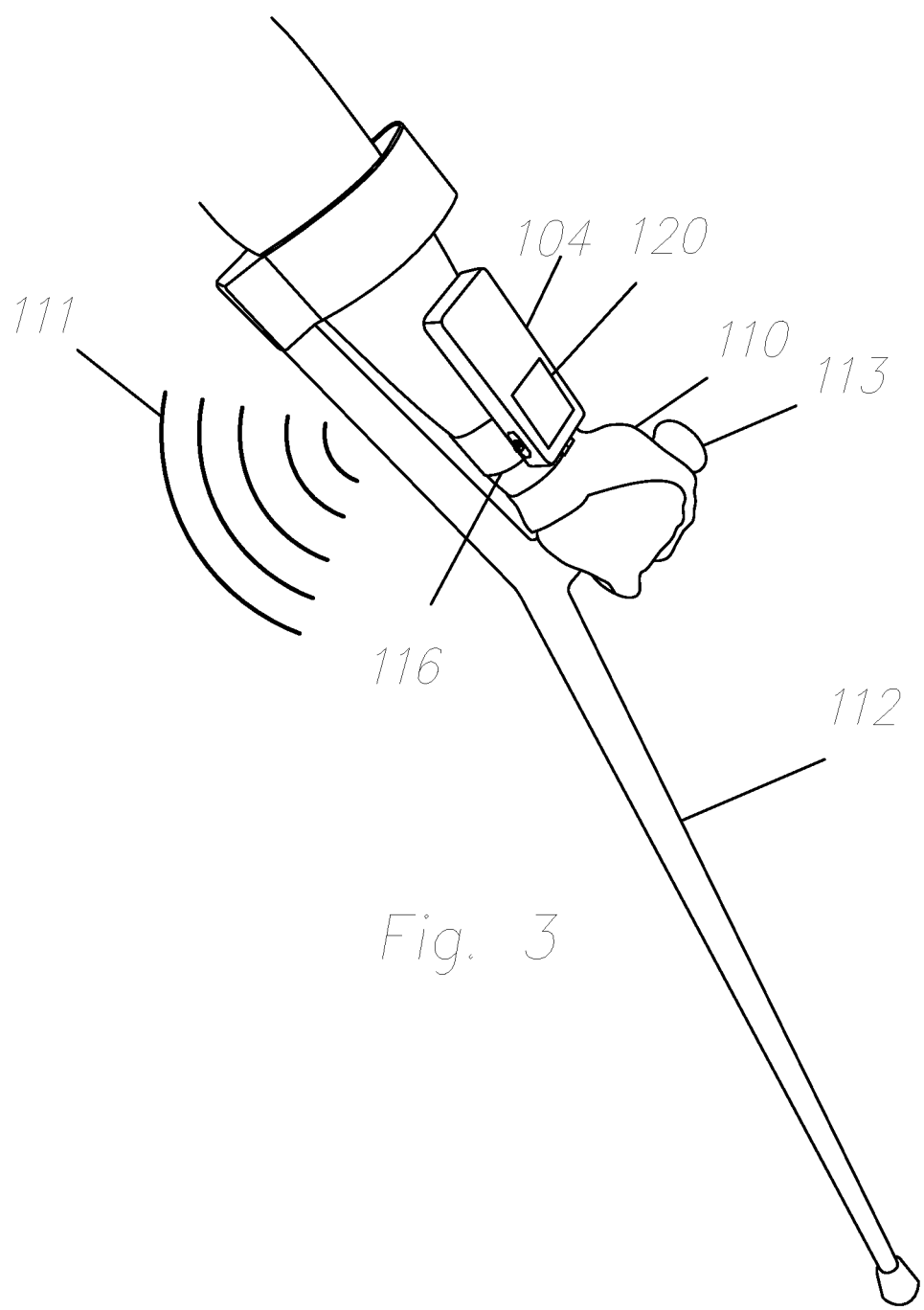
FIG. 3 depicts a user using the present invention in conjunction with crutches.
Figure 6:
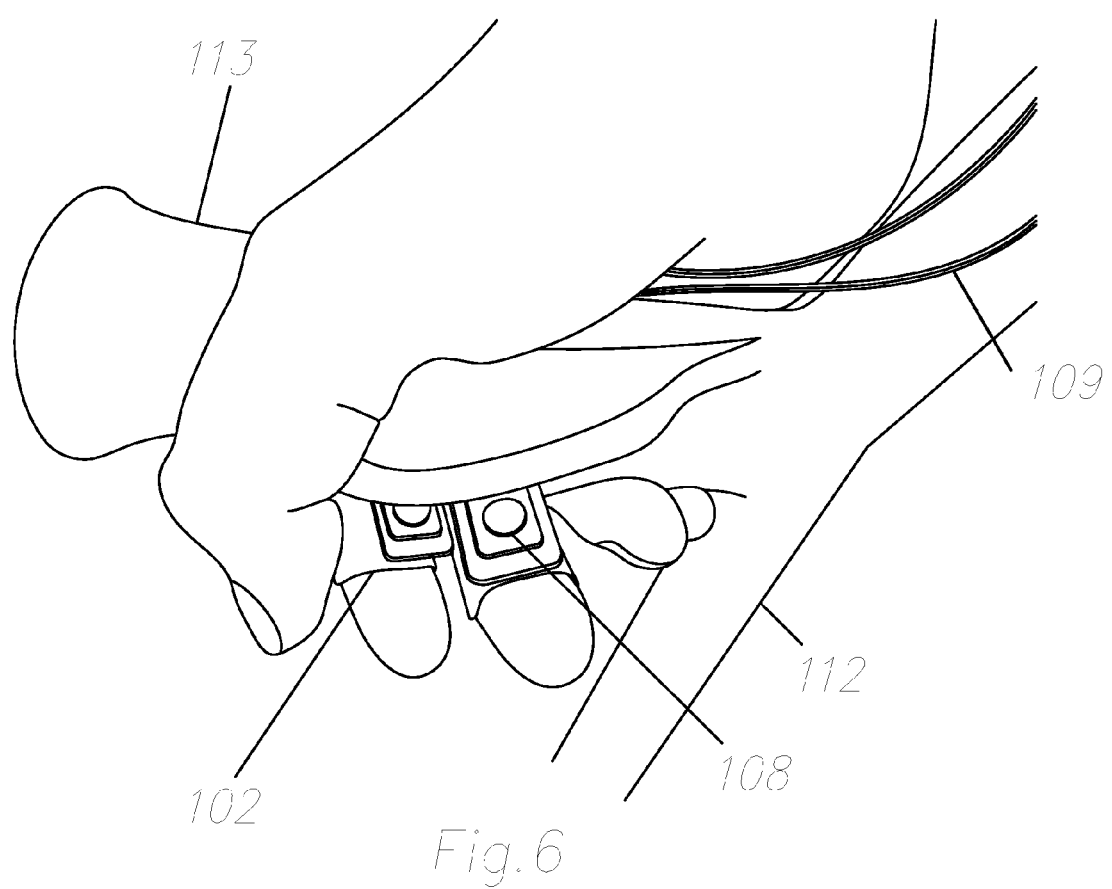
FIG. 6 depicts a possible way in which a user would use the present invention, contacting a crutch.

In some embodiments of the invention, an electric signal may be generated when the wearer contacts a signal generator 102 with a crutch 112, as shown in FIG. 2 and FIG. 3. When the person contacts crutch handle 113, shown in FIG. 6, and pushes against crutch handle 113 through signal generator 102, signal generator 102 generates at least one electric signal. Although FIG. 2 shows that input device 100 is coupled to the person wearing exoskeleton 130, as noted above, in some embodiments of the invention, input device 100 can be coupled to a practitioner and the practitioner can generate at least one command signal 111 to command exoskeleton 130 while it is worn by a separate wearer. As previously mentioned, in some embodiments of the invention, at least one electric signal is transmitted through a wire 109 to input device controller 104. Input device controller 104 receives the electric signal and transmits a command signal 111 to exoskeleton 130. In some embodiments, command signal 111 comprises any single or combination of signals selected from the group consisting of a signal representing the desired velocity of exoskeleton 130, a signal representing the desired acceleration of exoskeleton 130, and a signal representing the orientation of exoskeleton 130.

Figure 4:
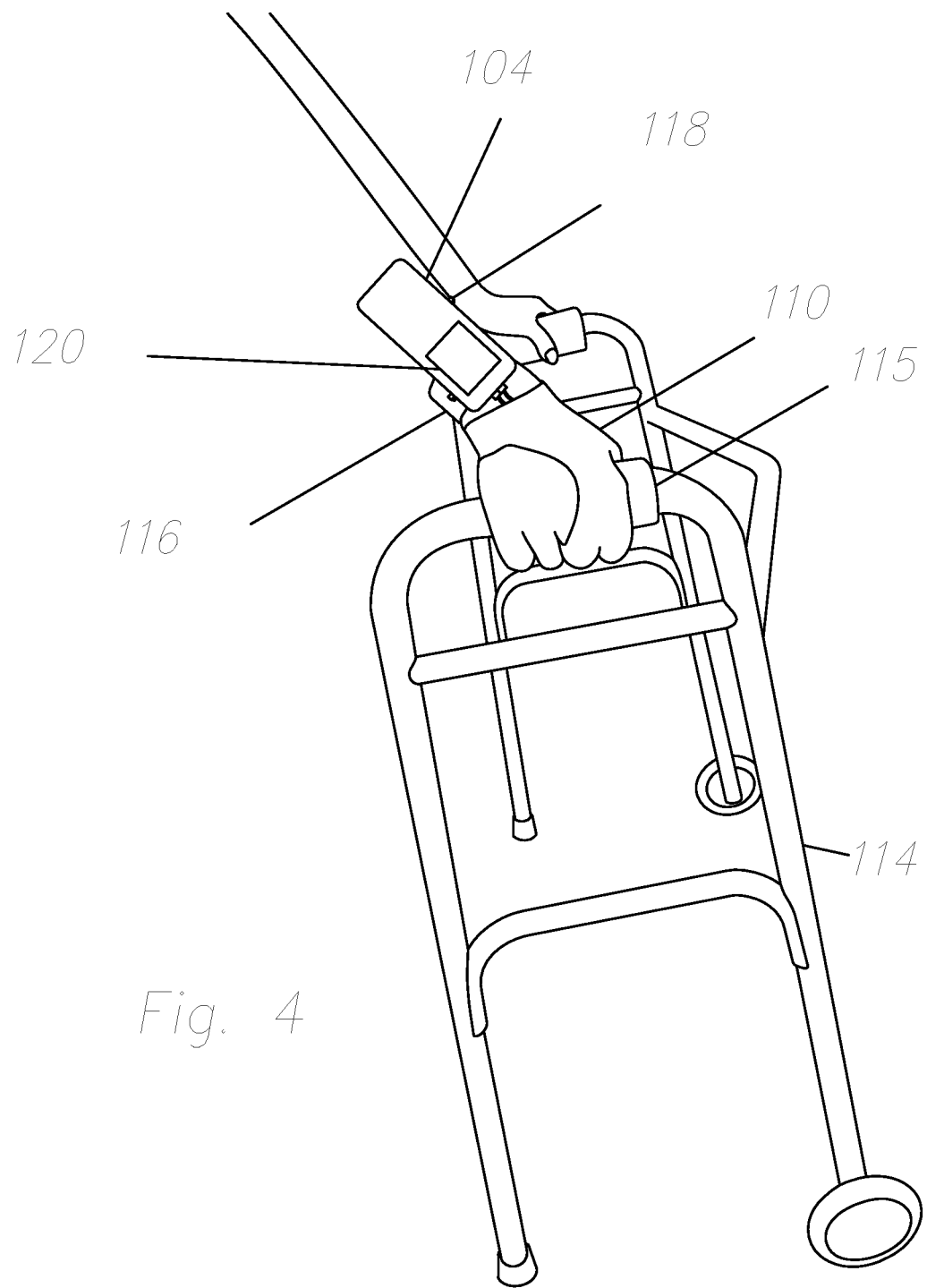
FIG. 4 depicts a user using the present invention in conjunction with a walker.
Figure 7:
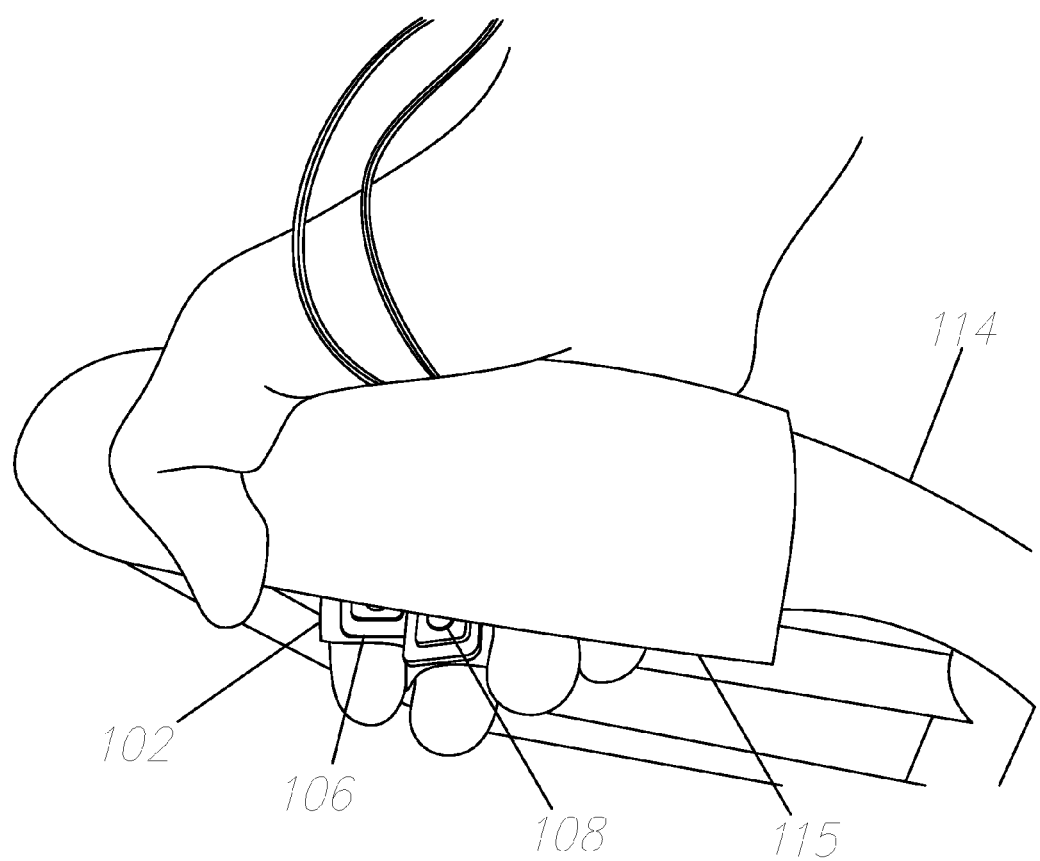
FIG. 7 depicts a possible way in which a user would use the present invention, contacting a walker.

Some individuals may like to use a walker 114 when operating an exoskeleton 130. In some embodiments of the invention, where walker 114 is used in conjunction with an exoskeleton 130, as shown in FIG. 4, the person contacts a walker handle 115 with the at least one signal generator 102 to generate the electric signal. When the signal generator 102 contacts the walker handle 115 and pushes against walker handle 115 through signal generator 102, as shown in FIG. 7, signal generator 102 generates at least one electric signal. In some embodiments of the invention, at least one electric signal is transmitted through a wire 109 to input device controller 104. Input device controller 104 receives the electric signal and transmits a command signal 111 to exoskeleton 130. Although not shown, some individuals may like to use a cane or parallel bars instead of a walker when operating an exoskeleton 130. It should be understood that the input device 100 of the present invention can be utilized with the supporting surface or handle of any balancing aid or means for supporting an exoskeleton user, including a crutch 112, a walker 114, a cane, parallel bars or other well-known balancing aids for supporting a powered medical exoskeleton user. Further embodiments of the invention contain components similar to those described previously.

In some embodiments of the invention, the command signal 111 generated by signal generator 102 represents a force between the wearer's finger and the contacting object, such as walker, crutches, or parallel bars.

Figure 5:
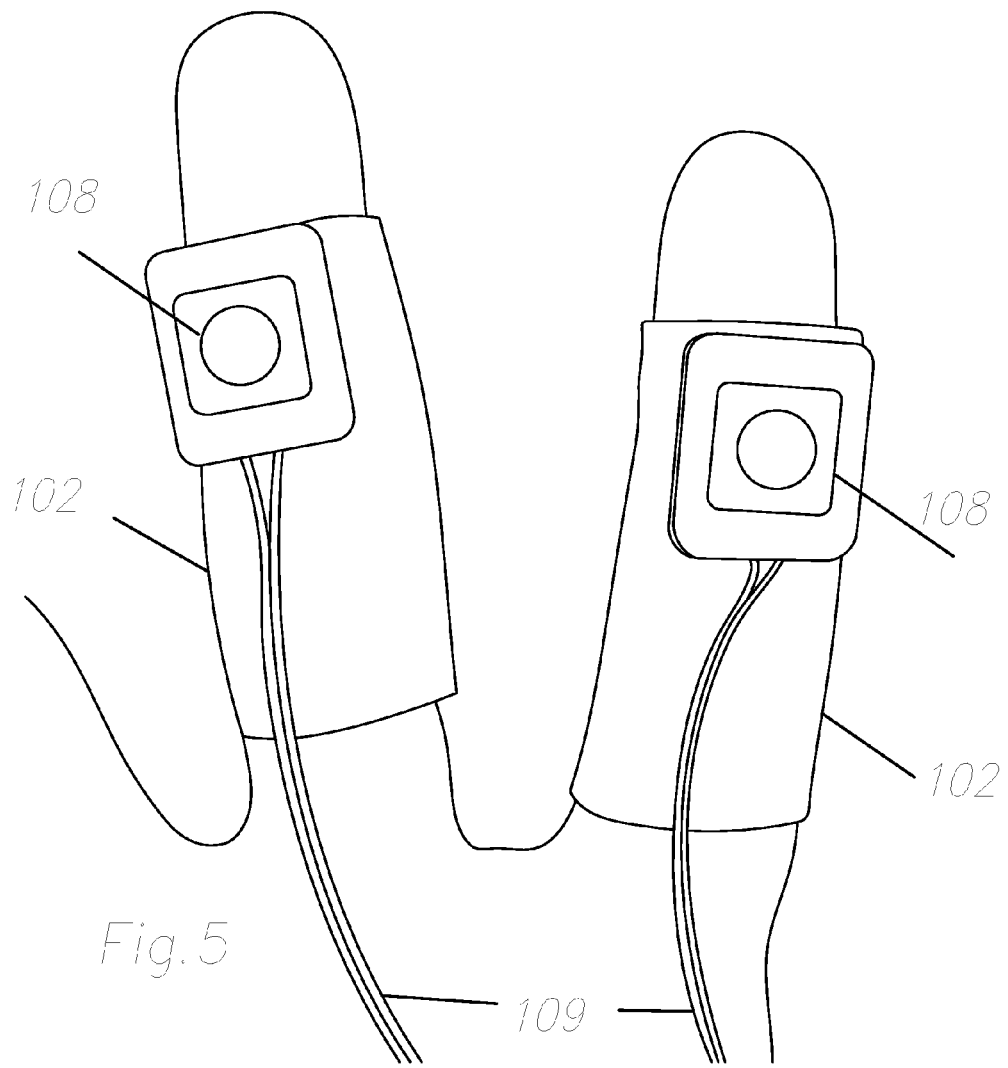
FIG. 5 depicts the signal generators without the rest of the present invention, for clarity.

The actuators of signal generators 102 may comprise an element or combination of elements selected from the group consisting of: pushbuttons, switches, including momentary switches, rocker switches, sliding switches, capacitive switches, and resistive switches, thumbwheels, thumb balls, roll wheels, track balls, keys, knobs, potentiometers, encoders, force sensors, strain gauge forces sensor and linear variable differential transformers (LVDTs). FIG. 5 shows an embodiment of the invention where signal generator comprises an actuator 108, such as a pushbutton. In some embodiments of this invention, signal generators 102 may be coupled to a person's finger via an element or combination of elements selected from the group consisting of sleeves, straps, rings, tapes, bands, and clips.

Figure 8:
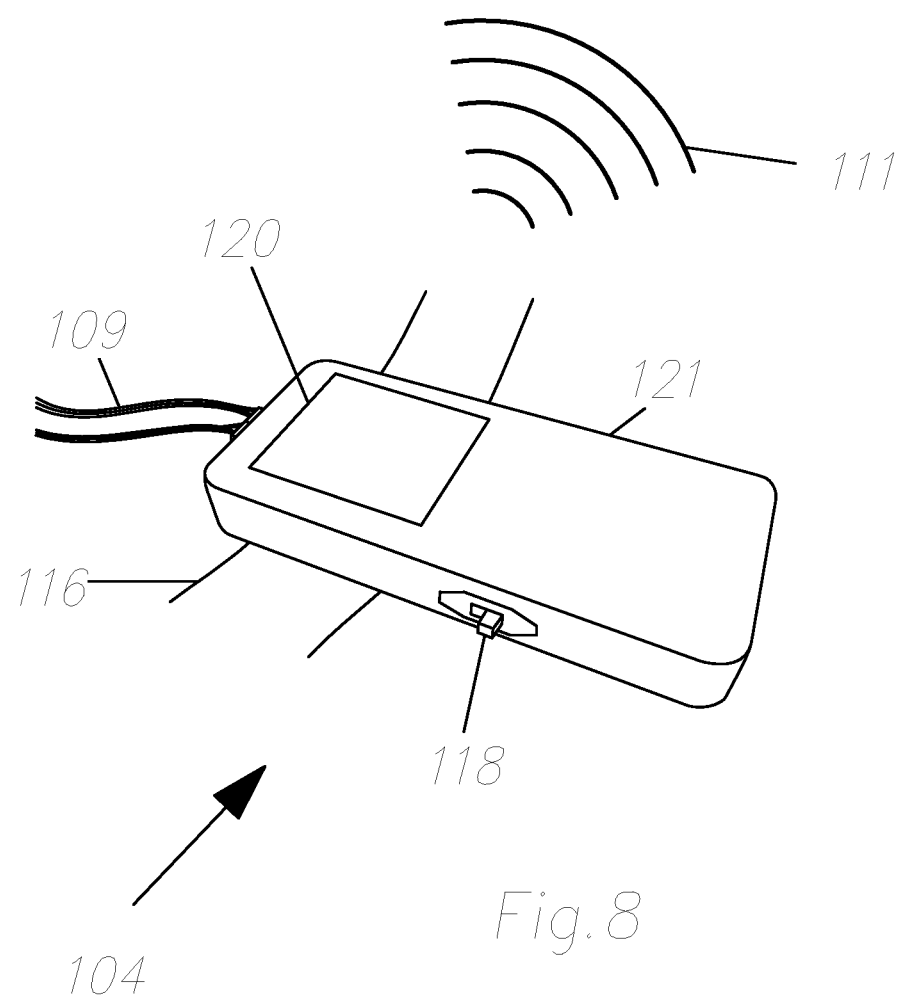
FIG. 8 depicts the input device controller of the present invention without the other components, for clarity.

FIG. 8 shows an embodiment of input device controller 104. Input device controller 104 is adapted to be coupled to a person's body 107. In some embodiments of the invention, input device controller 104 may be coupled to the person's body 107 via an element or a combination of elements selected from the group consisting of: bands, straps, tapes, clips, chains, rings, and belts. In operation, input device controller 104 receives and processes at least one electric signal from signal generator 102 and transmits a command signal 111 to exoskeleton 130. In some embodiments of the invention input device controller 104 comprises a housing 121.

In some embodiments of the invention, as shown in FIG. 1a through FIG. 4, input device controller 104 is coupled to a person's wrist. In some embodiments of the invention, command signal 111 generated by input device controller 104 is transmitted to exoskeleton 130 wirelessly. In some embodiments of the invention, the electric signal may be generated when the wearer contacts at least one signal generator 102 with a surface of a walker 114, a crutch 112, parallel bars, a cane, or other balancing aid. In some embodiments of the invention, command signal 111 generated by input device controller 104 initiates a motion in exoskeleton 130. In some embodiments of the invention, command signal 111 generated by input device controller 104 stops exoskeleton 130. In some embodiments of the invention, command signal 111 generated by input device controller 104 causes exoskeleton 130 to increase its locomotion speed. In some embodiments of the invention, command signal 111 generated by input device controller 104 causes exoskeleton 130 to slow down its locomotion speed. In some embodiments of the invention, command signal 111 generated by input device controller 104 causes exoskeleton 130 to shift between various operational states, such as seated, standing, and walking states.

Figure 9:
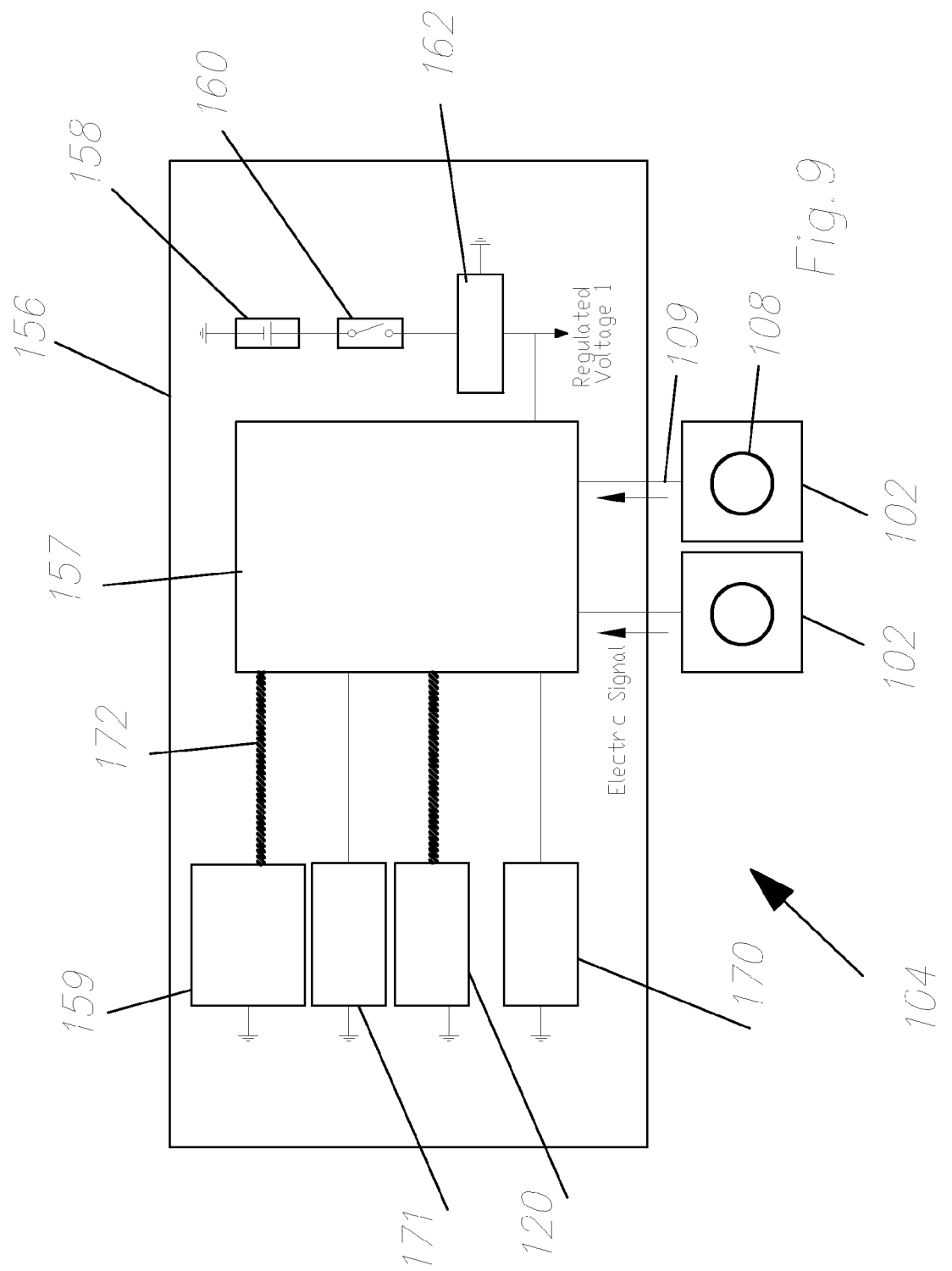
FIG. 9 depicts a schematic of the input device controller unit of the present invention.

FIG. 9 shows an embodiment of schematic of input device controller 104. In some embodiments of the invention, input device controller 104 comprises at least one printed circuit board (PCB) 156. PCB 156 holds many components of input device controller 104. In some embodiments of the invention input device controller 104 comprises at least one microcomputer 152, a wireless transceiver module 154, a battery 158, and a housing 121. In some embodiments, microcomputer 152 is an eight-bit Arduino Pro Mini manufactured by Arduino Co. Signal generator 102 is connected to input pins of the microcomputer 152. When an actuator 108 of a signal generator 102 is pressed against a balancing aid handle 113, microcomputer 152 receives an electric signal through wire 109 indicating that the user has pushed against handle 113 and activated the actuator. When actuator 108 is not activated, microcomputer 152 receives another electric signal through wire 109 indicating that signal generator 102 is not pressed against handle 113. Microcomputer 152 sends a computer command signal to transceiver module 154 mounted on PCB 156 using a serial communication port 172 indicating if actuator 108 has been activated or not. Wireless transceiver module 154 transmits command signal 111 to its paired module located on the exoskeleton controller 155. Transceiver module 154 used in the exemplary embodiment of the present invention is the XBee (series1) transmitter manufactured by Digi International. A battery 158 with proper voltage and current limit is also included in input device controller 104 to power all components of input device controller 104. Power switch 160 switches power on or off of input device controller 104.

In some embodiments of the invention, exoskeleton 130 is capable of sending a feedback signal to input device controller 104 for processing, wherein the feedback signal represents the exoskeleton's status. In some embodiments of the invention input device controller 104 further comprises a display 120. In operation, display 120 shows the status of input device controller 104 or exoskeleton 130 to the user. In some embodiments of the invention display 120 displays the status of input device controller 104 or exoskeleton 130 with an element or combination of elements selected from the group consisting of: text, still image, animation, and video clips.

In some embodiments of the invention input device controller 104 further comprises a vibrating motor 170. In operation, vibrating motor 170 provides tactile sensation related to the status of exoskeleton 130 or input device controller 104 to the user with an element or combination of elements selected from the group consisting of continuous, short term intermittent, and long term intermittent vibration.

In some embodiments of the invention input device controller 104 further comprises at least one speaker 171. In operation, speaker 171 generates audible sound related to the status of exoskeleton 130 or input device controller 104 to the user.

In some embodiments of the invention input device 100 comprises of at least one signal generator 102 and input device controller 104 can be coupled to a practitioner and the practitioner can generate at least one signal to command exoskeleton 130. In some embodiments of the invention, signal generator 102 can be coupled to a practitioner and input device controller 104 can be coupled to a person wearing exoskeleton 130.

In some embodiments of the invention, signal generator 102 coupled to a person's finger can generate at least one electric signal when signal generator 102 contacts another finger. Further embodiments of the invention contain components similar to those described previously.

FIG. 10 shows another embodiment of the invention. Input device 200 of the present invention is adapted to be coupled to a person's hand. The device comprises: an instrumented glove 110 which is adapted to be coupled to the person's hand. Instrumented glove 110 further comprises at least one signal generator 102 (not shown) coupled to one of the glove's digits. Similar to the embodiment depicted in FIG. 1a, the signal generator 102 utilized with input device 200 is capable of generating at least one electric signal when a person's finger contacts an object, such as a balancing aid (not shown). Input device 200 also comprises an input device controller 104, adapted to be coupled to said person's body 107. In operation, input device controller 104 receives and processes at least one electric signal and transmits a command signal to exoskeleton 130. In some embodiments, a wire 109 transmits at least one electric signal. In some embodiments of the invention, two signal generators 102 can be coupled to a finger. Input device 200 can utilize any desired number of signal generators 102. As with the embodiment shown in FIG. 1a, input device controller 104 of input device 200 may transmit a command signal 111 wirelessly, or via one or more wires, to exoskeleton 130. It should be understood that, in the context of the present invention, the term glove is intended to mean a flexible covering that encloses at least a portion of the user's palm and least one finger. In some embodiments of the invention, glove 110 covers at least one finger as depicted in FIG. 10. Further embodiments of the invention contain components similar to those described previously.

Although described with reference to a preferred embodiment of the invention, it should be readily understood that various changes and/or modifications can be made to the invention without departing from the spirit thereof. For instance, it should be understood that exoskeleton 130 can be any known powered exoskeleton device adapted for use with the present invention. In general, the invention is only intended to be limited by the scope of the following claims.

We claim:

1. A system for operating an exoskeleton comprising:
   an exoskeleton including:
   first and second leg supports configured to be coupled to a user's lower limbs, each of the first and second leg supports including a thigh link;
   an exoskeleton trunk configured to be coupled to a user's upper body, said exoskeleton trunk being rotatably connected to each of the first and second leg supports to allow for the flexion and extension between said first and second leg supports and said exoskeleton trunk;
   first and second powered actuators coupled to respective first and second leg supports, said first and second actuators configured to provide movement of the leg supports relative to said exoskeleton trunk;
   a support device separate from the exoskeleton to be held by a user of the exoskeleton, said support device comprising at least one support handle adapted to be grasped by a user's hand;
   an exoskeleton controller configured to shift said exoskeleton among a plurality of operational states and to receive user command signals; and
   a user input device for commanding said exoskeleton, said input device-including:
      a signal generator adaptable to be coupled to said user's finger, when the user's hand is in weight-bearing engagement with said support handle, so that said signal generator generates at least one electric signal when said user grasps said at least one support handle and said user's finger selectively contacts said signal generator against said at least one support handle without interfering with the weight-bearing engagement of the user's hand, and
      an input device controller adaptable to be coupled to said user's body capable of receiving said at least one signal from said signal generator, processing said at least one signal and transmitting said user command signals to said exoskeleton controller, said input device controller having an element or combination of elements selected from the group consisting of a display, a vibrating motor, and a speaker so that said input device controller is capable of generating visual information, tactile sensation, and/or audible sound related to said exoskeleton and/or said input device controller's status.

2. The system of claim 1, wherein said signal generator has an actuator comprising an element or combination of elements selected from the group consisting of pushbuttons, switches including momentary switches, rocker switches, sliding switches, capacitive switches, resistive switches, thumbwheels, thumb balls, roll wheels, track balls, keys, knobs, potentiometers, encoders, force sensors, stain gauge forces sensor and linear variable differential transformers.

3. The system of claim 1, wherein said signal generator is coupled to a user's finger via an element or a combination of elements selected from the group consisting of sleeves, straps, metal rings, plastic rings, tapes, and clips.

4. The system of claim 1, wherein said signal generator transmits said at least one signal to said input device controller via at least one wire.

5. The system of claim 1, wherein said input device controller is coupled to said user's body via an element or a combination of elements selected from the group consisting of straps, bands, tapes, clips, chains, rings, and belts.

6. The system of claim 1, wherein said input device controller comprises a microcomputer, at least one battery and a wireless transceiver module capable of wirelessly sending said command signal to said exoskeleton.

7. The system of claim 1, wherein said command signal initiates a motion in said exoskeleton.

8. The system of claim 1, wherein said command signal stops a motion in said exoskeleton.

9. The system of claim 1, wherein said command increases said exoskeleton's speed.

10. The system of claim 1, wherein said command signal decreases said exoskeleton's speed.

11. The system of claim 1, wherein said command signal causes a change in configuration of said exoskeleton.

12. The system of claim 1, wherein said exoskeleton is capable of sending at least one feedback signal to said input device controller for processing, wherein said feedback signal represents said exoskeleton's status.

13. The system of claim 1, wherein said signal generator is integrated into a glove wherein said glove is adapted to be worn by said user.

14. The system of claim 1, wherein the user input device controller includes a display for displaying visual information selected from the group consisting of text, still image, animation, video clips, and a combination thereof.

15. A control method of an exoskeleton utilizing the system of claim 1; said control method comprising the steps of:
   when the user's hand is in weight-bearing engagement with the support handle, generating at least one signal by contacting the support handle with said signal generator in said glove without interfering with the weight-bearing engagement of the user's hand;
   processing said signal in said input device controller;

generating a command signal for said exoskeleton in said input device controller;

transmitting said command signal to the exoskeleton controller to cause, change, or inhibit motion in said exoskeleton; and generating visual information, tactile sensation, and/or audible sound related to said exoskeleton and/or said input device controller's status on the glove.

16. The method claim of 15, where the said signal generated by said signal generator represents a force between said user's finger and said handle.

17. The method claim of 15, wherein said signal generator has an actuator comprising an element or combination of elements selected from the group consisting of pushbuttons, switches including momentary switches, rocker switches, sliding switches, capacitive switches, resistive switches, thumbwheels, thumb balls, roll wheels, track balls, keys, knobs, potentiometers, encoders, force sensors, stain gauge forces sensor and linear variable differential transformers.

18. The method claim of 15, where the said command signal is transmitted wirelessly.

19. The method claim of 15, wherein said command signal comprises any single or combination of signals selected from the group consisting of a signal representing the desired velocity of said exoskeleton, a signal representing the desired acceleration of said exoskeleton, and a signal representing the orientation of said exoskeleton.

20. The method of claim 15, wherein visual information is generate and displayed on a display of the input device, wherein the visual information is selected from the group consisting of text, still image, animation, video clips, and a combination thereof.

* * * * *